US012059527B2

(12) United States Patent
Tseng et al.

(10) Patent No.: US 12,059,527 B2
(45) Date of Patent: Aug. 13, 2024

(54) METHOD FOR DRIVING NEBULIZER AND CIRCUIT SYSTEM

(71) Applicant: MICROBASE TECHNOLOGY CORP., Taoyuan (TW)

(72) Inventors: Hsin-Hua Tseng, Taoyuan (TW); Chih-Wei Lu, Taoyuan (TW); Chen-Hsiang Sang, Taoyuan (TW); Liang-Rern Kung, Taoyuan (TW); Jo-Ling Wu, Taoyuan (TW); Shu-Pin Hsieh, Taoyuan (TW)

(73) Assignee: MICROBASE TECHNOLOGY CORP., Taoyuan (TW)

( * ) Notice: Subject to any disclaimer, the term of this patent is extended or adjusted under 35 U.S.C. 154(b) by 723 days.

(21) Appl. No.: 17/147,552

(22) Filed: Jan. 13, 2021

(65) Prior Publication Data

US 2021/0128854 A1 May 6, 2021

Related U.S. Application Data

(63) Continuation of application No. PCT/CN2019/095997, filed on Jul. 15, 2019.
(Continued)

(51) Int. Cl.
*A61M 16/00* (2006.01)
*A61M 15/00* (2006.01)
(Continued)

(52) U.S. Cl.
CPC ...... *A61M 16/024* (2017.08); *A61M 15/0085* (2013.01); *A61M 16/14* (2013.01);
(Continued)

(58) Field of Classification Search
CPC .. A61M 16/024; A61M 16/022; A61M 16/00; A61M 2016/0015; A61M 15/0085; A61M 2205/3375
See application file for complete search history.

(56) References Cited

U.S. PATENT DOCUMENTS 3,724,454 A 4/1973 Brown
5,364,838 A 11/1994 Rubsamen
(Continued)

FOREIGN PATENT DOCUMENTS

CN 1738666 A 2/2006
CN 101850145 A 10/2010
(Continued)

OTHER PUBLICATIONS

European Patent Office, Search Report issued on Mar. 10, 2022 for EP application No. 19837007.4.
WIPO, International Search Report issued on Sep. 2, 2019.

*Primary Examiner* — Margaret M Luarca
*Assistant Examiner* — Sarah B Lederer
(74) *Attorney, Agent, or Firm* — Li & Cai Intellectual Property (USA) Office

(57) ABSTRACT

A method and a circuit system for driving a nebulizer are provided. When the nebulizer receives acoustic waves, a control circuit extracts audio signals from the acoustic waves. Afterwards, the control circuit determines if the audio signals are within a predetermined frequency range, and can determine whether or not to drive a circuit to produce an aerosol based on the audio signals. Further, a volume of the acoustic waves can also be used to determine whether or not to produce the aerosol, and also determine an output rate of the aerosol. The circuit system of the nebulizer includes an audio receiver for receiving the acoustic waves, an aerosol generator for producing the aerosol, and the control circuit used to control a driving circuit of the aerosol generator to drive a vibrational element to produce the aerosol through vibration in response to the audio signals and the volume.

16 Claims, 7 Drawing Sheets

Related U.S. Application Data

(60) Provisional application No. 62/698,988, filed on Jul. 17, 2018.

(51) Int. Cl.
*A61M 16/14* (2006.01)
*G08C 23/02* (2006.01)
*G10L 25/51* (2013.01)
*G16H 20/13* (2018.01)

(52) U.S. Cl.
CPC .............. *G08C 23/02* (2013.01); *G10L 25/51* (2013.01); *G16H 20/13* (2018.01); *A61M 2016/0021* (2013.01); *A61M 2205/3375* (2013.01)

(56) References Cited

U.S. PATENT DOCUMENTS

| | | | |
|---|---|---|---|
| 5,458,135 | A | 10/1995 | Patton et al. |
| 8,474,452 | B2 | 7/2013 | Gumaste et al. |
| 9,352,107 | B2 | 5/2016 | Von Hollen et al. |
| 10,046,121 | B2 | 8/2018 | Kolb et al. |
| 10,258,753 | B2 | 4/2019 | Adams et al. |
| 2005/0183725 | A1* | 8/2005 | Gumaste ............... A61M 15/02 128/203.15 |
| 2006/0102172 | A1 | 5/2006 | Feiner et al. |
| 2014/0000597 | A1 | 1/2014 | Korneff |
| 2014/0166004 | A1 | 6/2014 | Pierro et al. |
| 2015/0114409 | A1 | 4/2015 | Brammer et al. |
| 2016/0199593 | A1 | 7/2016 | Morrison et al. |
| 2016/0228656 | A1 | 8/2016 | Vasandani et al. |
| 2018/0161530 | A1 | 6/2018 | Ganton et al. |

FOREIGN PATENT DOCUMENTS

| | | | |
|---|---|---|---|
| CN | 1925887 B | 12/2010 | |
| CN | 102695535 A | 9/2012 | |
| CN | 104010685 A | 8/2014 | |
| CN | 104870038 A | 8/2015 | |
| CN | 105413026 A | 3/2016 | |
| CN | 105473175 A | 4/2016 | |
| CN | 106512157 A | 3/2017 | |
| CN | 206214533 U | 6/2017 | |
| TW | 201609272 A | 3/2016 | |
| WO | WO-9707896 A1 * | 3/1997 | .......... A61M 11/005 |
| WO | WO 9707896 A1 | 3/1997 | |
| WO | WO 9964095 A2 | 12/1999 | |
| WO | WO 2011153406 A2 | 12/2011 | |

* cited by examiner

METHOD FOR DRIVING NEBULIZER AND CIRCUIT SYSTEM

CROSS-REFERENCE TO RELATED PATENT APPLICATION

This application is a continuation application of International Patent Application Ser. No. PCT/CN2019/095997, filed on Jul. 15, 2019, which claims the priority of the U.S. Provisional Patent Application Ser. No. 62/698,988, filed on Jul. 17, 2018. The entirety of each of the above patent applications is hereby incorporated by reference herein and made a part of this specification.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The disclosure is related to a technology for driving a nebulizer, and more particularly to a method for deciding an operating timing to drive the nebulizer according to an audio signal and a circuit system thereof.

BACKGROUND OF THE DISCLOSURE

A nebulizer is an electronic device that can nebulize liquid medicine loaded in the device into an aerosol by vibration. The liquid medicine forms fine aerosols through rapid vibration. The nebulized medicine can then be inhaled through a mouth of a user, so as to achieve the effect of treating a specific illness.

A conventional nebulizer can be manually turned off or turned on during operation. However, the conventional nebulizer may lead to wasting of medicine and electricity if it continues to operate without having any mechanism that effectively controls the on/off state thereof.

SUMMARY OF THE DISCLOSURE

The method of the present disclosure makes a nebulizer to provide aerosol more effectively. Provided in the present disclosure is a method for driving a nebulizer and a circuit system thereof, which allow the nebulizer to provide an aerosol more effectively. One inventive concept described herein allows the nebulizer itself to determine an operating timing according to audio signals received in real time.

According to an embodiment of the method for driving the nebulizer, the nebulizer includes an audio receiver that receives acoustic waves and excerpts the audio signals from the acoustic waves. A control circuit determines whether or not the nebulizer produces the aerosol according to the audio signals.

Further, in one aspect, when the audio receiver receives the acoustic waves, the control circuit determines whether or not the audio signals are within a predetermined frequency range. An aerosol generator of the nebulizer is driven to produce the aerosol if the audio signals are determined to be within the predetermined frequency range.

In another aspect, the audio receiver is configured to receive the audio signals within a predetermined frequency range. In other words, other than the acoustic waves that are within the predetermined frequency range, acoustic waves of other ranges will not be used to drive anything. Thus, the control circuit of the nebulizer drives the aerosol generator to produce the aerosol if the audio receiver receives the audio signals that are within the predetermined frequency range.

Moreover, when the nebulizer acquires the audio signals obtained from the acoustic waves, a volume of the acoustic waves can also be obtained. The control circuit of the nebulizer determines whether or not to produce the aerosol according to the audio signals and the volume.

Further, the volume obtained can be compared with a predetermined threshold. That is, the volume acts as a factor provided for the control circuit to determine whether or not the aerosol generator is driven to produce the aerosol. In one aspect, the volume can be used as a reference to control an output rate of the aerosol.

According to one embodiment of a circuit system for performing the method for driving the nebulizer, one of the main components of the circuit system of the nebulizer is an audio receiver that is disposed on the path along which an airflow passes for receiving the acoustic waves. For example, the audio receiver can be disposed at an aerosol outlet. Another component of the circuit system is an aerosol generator used to produce the aerosol. One more component of the circuit system is a control circuit that is used to control operations of the nebulizer. The control circuit determines whether or not to drive the aerosol generator to produce the aerosol in response to the audio signals obtained from the acoustic waves.

The nebulizer further includes an audio generator. The audio generator can be a circuit, or can be a reed or an acoustic structure that is configured to receive the airflow passing the nebulizer and generate the audio signals within the predetermined frequency range.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings in which.

DETAILED DESCRIPTION OF THE EXEMPLARY EMBODIMENTS

Figure 1:
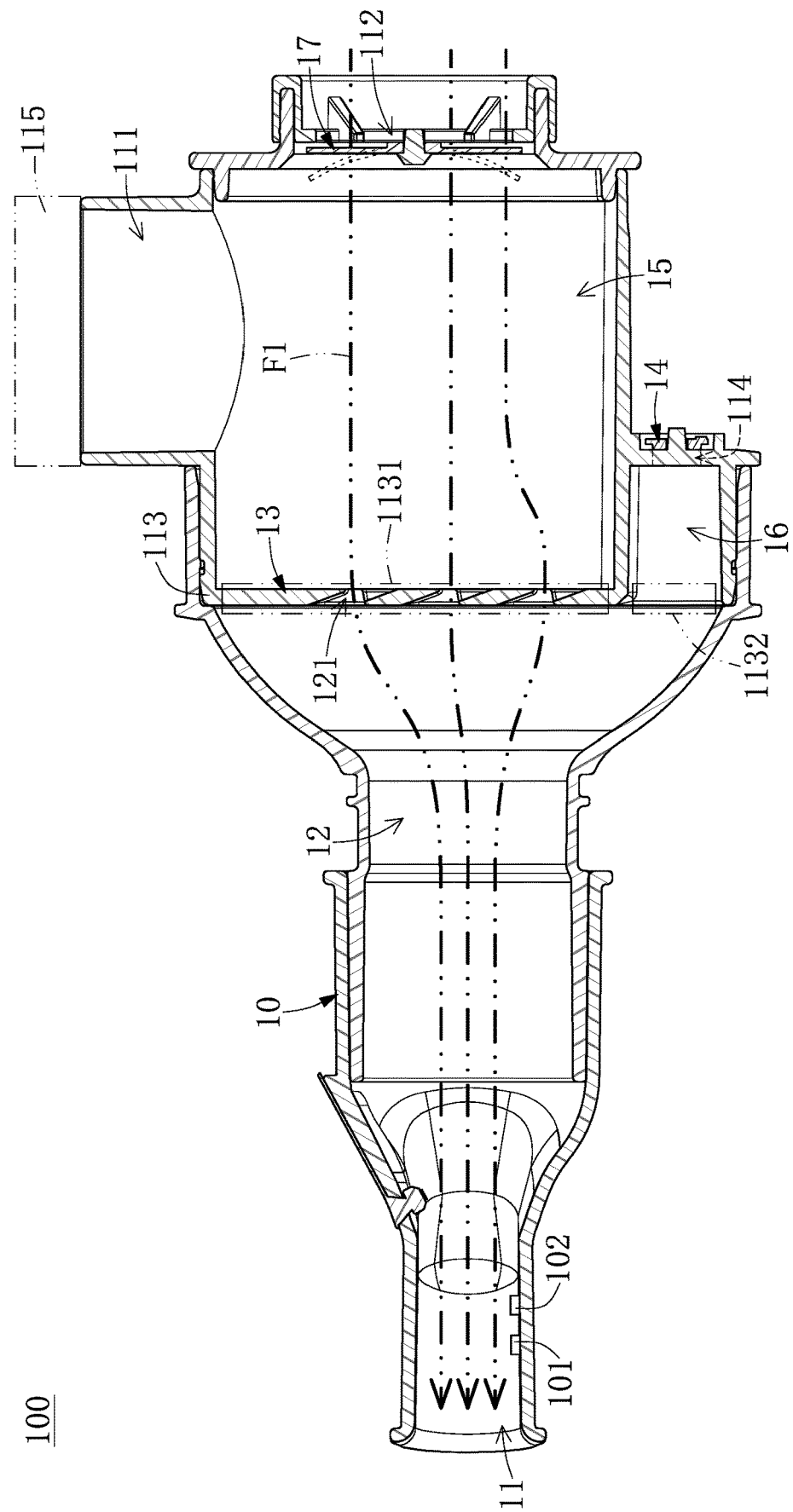
FIG. 1 is a schematic sectional view showing a structure of a nebulizer according to one embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

A nebulizer is a device that is used to nebulize liquid particles attached to aperture elements of a vibrational element by vibration, so as to produce an aerosol. The aerosol moves with an airflow. For example, the nebulizer can be a device to be held by a patient's mouth. The liquid particles are such as a medicine that can be administered to the patient after it is nebulized. The nebulizer can control energy of the vibration, e.g., vibration frequency or vibration amplitude, and adjust time to release the medicine. The nebulizer can precisely release the medicine during each use so as to accurately administer an effective dose of the medicine to the patient. Therefore, waste and risk caused by overuse of the medicine can be reduced. The present disclosure provides a method for driving the nebulizer and a circuit system for implementing the method. The circuit system determines a timing to drive the nebulizer to produce the aerosol in response to audio signals passing the nebulizer, so as to release the aerosol more effectively and without waste. The aerosol is such as nebulized pharmaceutical particles.

FIG. 1 and FIG. 2 each show a sectional schematic view of a structure of the nebulizer according to one embodiment of the present disclosure.

The main structure of the nebulizer 100 includes a breathing element 10 that has a mouthpiece 11 provided for a user to breathe through. The mouthpiece 11 forms an aerosol outlet of the nebulizer 100. The breathing element 10 is sleeved over an outlet used to release the aerosol generated by the nebulizer 100. As shown in the drawing, a splitting chamber 12 is disposed in front of an intake area 1131 and an exhaust area 1132 of the nebulizer 100. The splitting chamber 12 is connected to the breathing element 10 in the front, and is sleeved over a junction member 113 of a nebulization chamber 15 and an exhaust chamber 16 of the nebulizer 100 in the back. The splitting chamber 12 is used to split the passing airflow. For example, the splitting chamber 12 splits the inhaled airflow and the exhaled airflow of the user.

A splitting baffle 13 is disposed at the intake area 1131 of the nebulization chamber 15 that is near the breathing element 10. The splitting baffle 13 is used to separate the nebulization chamber 15 and the splitting chamber 12. The splitting baffle 13 has some apertures 12 that allow unidirectional airflow to pass through. In addition to the exhaust area 1132 near the breathing element 10, the exhaust chamber 16 has an exhaust port 114 at another side. The exhaust port 114 has an exhaust valve plate 14 that is used to control the unidirectional airflow so as to exhaust the airflow out of the exhaust chamber 16. Another side of the nebulization chamber 15 is a structure used for intake. The main structure of the nebulization chamber 15 is an intake valve plate 17 and an intake port 112 that are configured to control the unidirectional airflow.

The nebulizer 100 includes a nebulization member 115 that is used to produce an aerosol. The nebulization member 115 has an aerosol generator being driven by a control circuit. In one aspect, the aerosol generator includes a vibrator which generates the aerosol by vibration. The aerosol formed in the nebulization member 115 is exhausted to the nebulization chamber 15 via an aerosol inlet 111.

In the nebulizer 100 shown in FIG. 1, the airflow passing through the intake port 112, the intake valve plate 17, the nebulization chamber 15, the intake area 1131, the apertures 121 of the splitting baffle 13, the splitting chamber 12 and the mouthpiece 11 of the breathing element 10 in sequence forms a first airflow F1. The first airflow F1 embodies an inhalation phase that generates the airflow while the user's mouth covers the mouthpiece 11 to inhale the air. The first airflow F1 carries the aerosol in the nebulization chamber 15 to be inhaled by the user.

In the nebulizer 100 shown in FIG. 2, the airflow passing through the mouthpiece 11 of the breathing element 10, the splitting chamber 12, the exhaust chamber 16 via the exhaust area 1132, the exhaust port 114 and the exhaust valve plate 14 in sequence forms a second airflow F2. The second airflow F2 embodies an exhalation phase. The second airflow F2 is generated when the user's mouth holds the mouthpiece 11 to exhale. The second airflow F2 does not carry any aerosol into the user.

More particularly, according to the method for driving the aerosol provided herein, the embodiments illustrated in FIG. 1 and FIG. 2 show that the breathing element 10 of the nebulizer 100 includes an audio generator 101 and an audio receiver 102. It should be noted that the drawings are provided merely for illustrative purpose. In practice, the circuit system and the circuit components can be integrated into one system in the nebulizer 100.

According to one of the embodiments, the audio generator 101 can be a device or a structure specified to generate the audio signals within a predetermined frequency range via airflow with a specific direction, e.g., the first airflow F1. The structure for generating the audio signals is such as a reed or an acoustic structure. The structure allows the passing airflow to generate the audio signals within the predetermined frequency range. The audio receiver 102 can receive the acoustic waves generated from various environments, including acoustic waves generated by the audio generator 101, and the audio signals can be obtained (e.g., excerpted or extracted) from the acoustic waves.

The audio generator 101 can be driven by the airflow flowing in the nebulizer 100 so as to generate the audio signals within a specific frequency range. The audio signals can be separated from other signals in the environment. That is, the circuit system of the nebulizer 100 can drive the aerosol generator to produce the aerosol based on the audio signals. It should be noted that the audio generator 101 can be a specific device or structure that is able to cause the unidirectional airflow to generate the acoustic waves so as to obtain the audio signals. Conversely, the airflow with a different direction cannot generate the acoustic waves due to the specific device or structure, or can only generate signals with a non-predetermined frequency. Further, the audio signals can be used with a volume of the acoustic waves. For example, only the acoustic waves with sufficient energy can make the audio receiver 102 to work, and the circuit system can obtain the volume in order to drive the nebulizer to operate.

In one embodiment, the audio generator 101 may not be a requisite component of the nebulizer that only relies on the audio receiver 102 to receive the acoustic waves from the various environments, including internal airflows. The control circuit of the circuit system of the nebulizer then converts the acoustic waves into audio signals, and determines whether or not the audio signals are within the predetermined frequency range.

In another embodiment, the audio receiver can be configured to receive only the audio signals within the predetermined frequency range. Acoustic waves not within the predetermined frequency range will not be accepted, and the nebulizer 100 will not be driven to operate. Therefore, the control circuit of the nebulizer 100 drives the aerosol generator to produce an aerosol once the audio receiver 102 receives the audio signals within the predetermined frequency range.

As discussed above, the nebulizer provided herein relies on the acoustic waves to determine whether or not to work. Specifically, the audio signals can be obtained from the acoustic waves through a signal processing process. The audio signals can be indicative of a frequency of a vibration of sound, and the frequency is related to the design of the audio generator 101 of the nebulizer 100. A threshold thereof is incorporated into the circuit system that drives the nebulizer 100 to produce the aerosol for receiving the audio signals only within a specific range. The volume can also be obtained from the acoustic waves and the volume indicates amplitude of the acoustic waves. Since the amplitude has a positive relationship with the volume, the volume can be used to determine strength of the user's breathing A threshold thereof can be incorporated into the circuit system as a reference to determine whether or not to produce the aerosol.

In one embodiment, the circuit system used to implement the method for driving the nebulizer 100 is disposed in the nebulizer 100. The circuit system decides whether or not to adopt the audio generator 101 according to a practical need. The audio signals generated by the audio generator 101 can be distinguished from common environmental acoustic waves, and therefore a mis-operation can be prevented.

Alternatively, the range of the sound received by the audio receiver 102 can be controlled for distinguishing from the environmental acoustic waves. For example, the predetermined frequency range setting in the circuit system to determine whether or not to drive the nebulizer can be a common frequency range that is detectable by a human ear, or an ultrasonic frequency range that is undetectable by a human ear.

Figure 3:
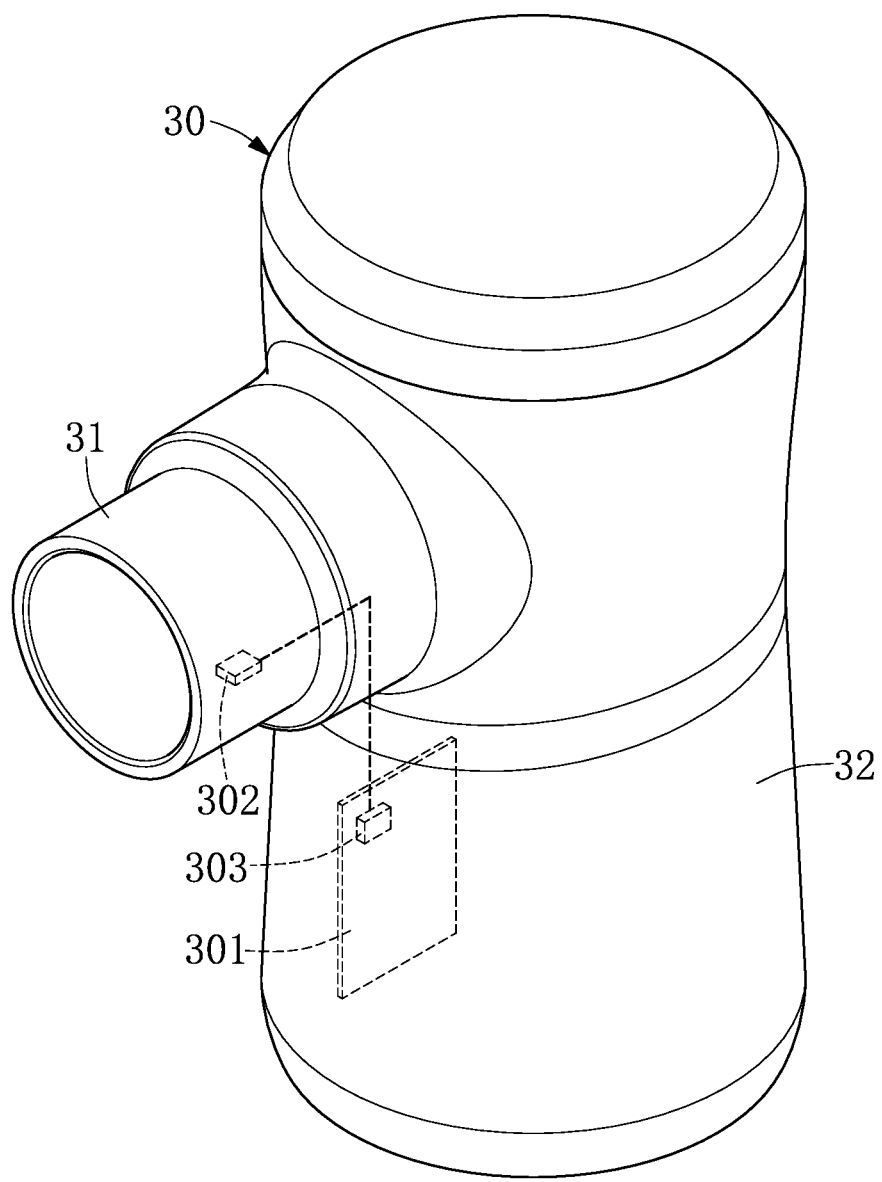
FIG. 3 is yet another schematic sectional view showing the structure of the nebulizer according to one embodiment of the disclosure.

FIG. 3 is a schematic view depicting another nebulizer according to one embodiment of the present disclosure. A nebulizer 30 is shown. The type and the components inside the nebulizer 30 can be adjusted according to practical requirements. The drawing should not be construed as limiting the scope of the present disclosure.

The main components of the nebulizer include an audio generator 302 and an audio receiver 303 that are interconnected. The audio generator 302 of the breathing element 31 can be any structural component or circuit component that can generate the acoustic waves (e.g., with a frequency or an amplitude) based on the passing airflow. The nebulizer 30 includes an audio receiver 303 that is disposed on a control circuit board 301 in a device body 32. The audio receiver 303 can be implemented by a circuit module or a software module that is used to convert the acoustic waves generated by the audio generator 302 into audio signals or a volume that acts as a reference for driving an operation of the nebulizer 30.

When the nebulizer 30 is in operation, the audio generator 302 of the breathing element 31 operates in response to exhalation or inhalation of the user. More particularly, during the user's inhalation to acquire the aerosol, the audio generator 302 generates acoustic waves based on the airflow and transmits the acoustic waves to the audio receiver 303. The audio receiver 303 cooperates with a control circuit to generate the audio signals and/or the volume.

Figure 4:
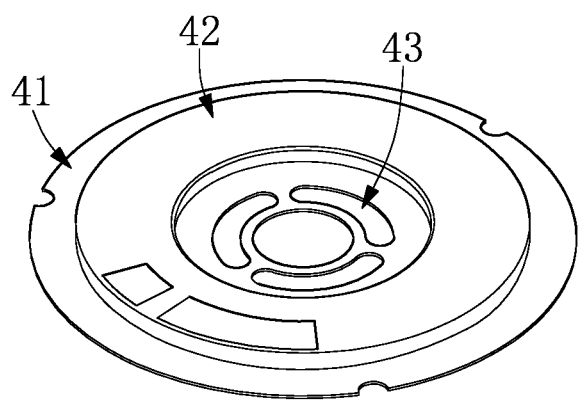
FIG. 4 is a schematic view showing an aerosol generator according to one embodiment of the present disclosure.

Reference is made to FIG. 4, which is a schematic view depicting an aerosol generator according to one embodiment of the disclosure.

The main components of the aerosol generator includes an external supporting structure 41, a vibrational element 42 used to generate vibration waves, an aperture element 43 that is able to carry tiny particles, and a driving circuit (not shown in the drawing). The drawing shows the main components of the nebulization member 115. The supporting structure 41 is disposed inside the nebulization member 115, and is connected to the vibrational element 42 and the aperture element 43. In the method for driving the nebulizer, the audio receiver is used to receive the acoustic waves, and the control circuit determines whether or not the audio signals obtained from the acoustic waves are within a predetermined frequency range. The driving circuit generates a vibration signal in order to drive the aerosol generator if the audio signals are within the predetermined frequency range. The control circuit can drive the vibrational element 42 to generate vibration waves with a specific frequency. The vibration waves can nebulize the liquid particles attached to the aperture element 43 by vibration. For example, in FIG. 1, the liquid particles are nebulized in the nebulization member 115 so as to form an aerosol. The aerosol is then exhausted to the nebulization chamber 15 via the aerosol inlet 111, and carried by the first airflow F1 to be administered to the user.

According to one embodiment, the audio generator of the nebulizer can be disposed on the path of airflow in the nebulizer. The audio generator may be disposed on the portion touching the user's mouth. The audio generator is configured to generate the audio signals with a specific frequency and volume. In one aspect of the disclosure, the frequency acts as a main factor for the nebulizer to determine whether or not to produce an aerosol. The volume acts as a second factor for determining whether or not to produce the aerosol. The audio generator can be a whistle, a dog whistle or a reed. The audio receiver is such as a microphone used for receiving the acoustic waves and then generating audio signals. The audio receiver can be a device that is configured to only receive the acoustic waves within a specific frequency range.

Figure 2:
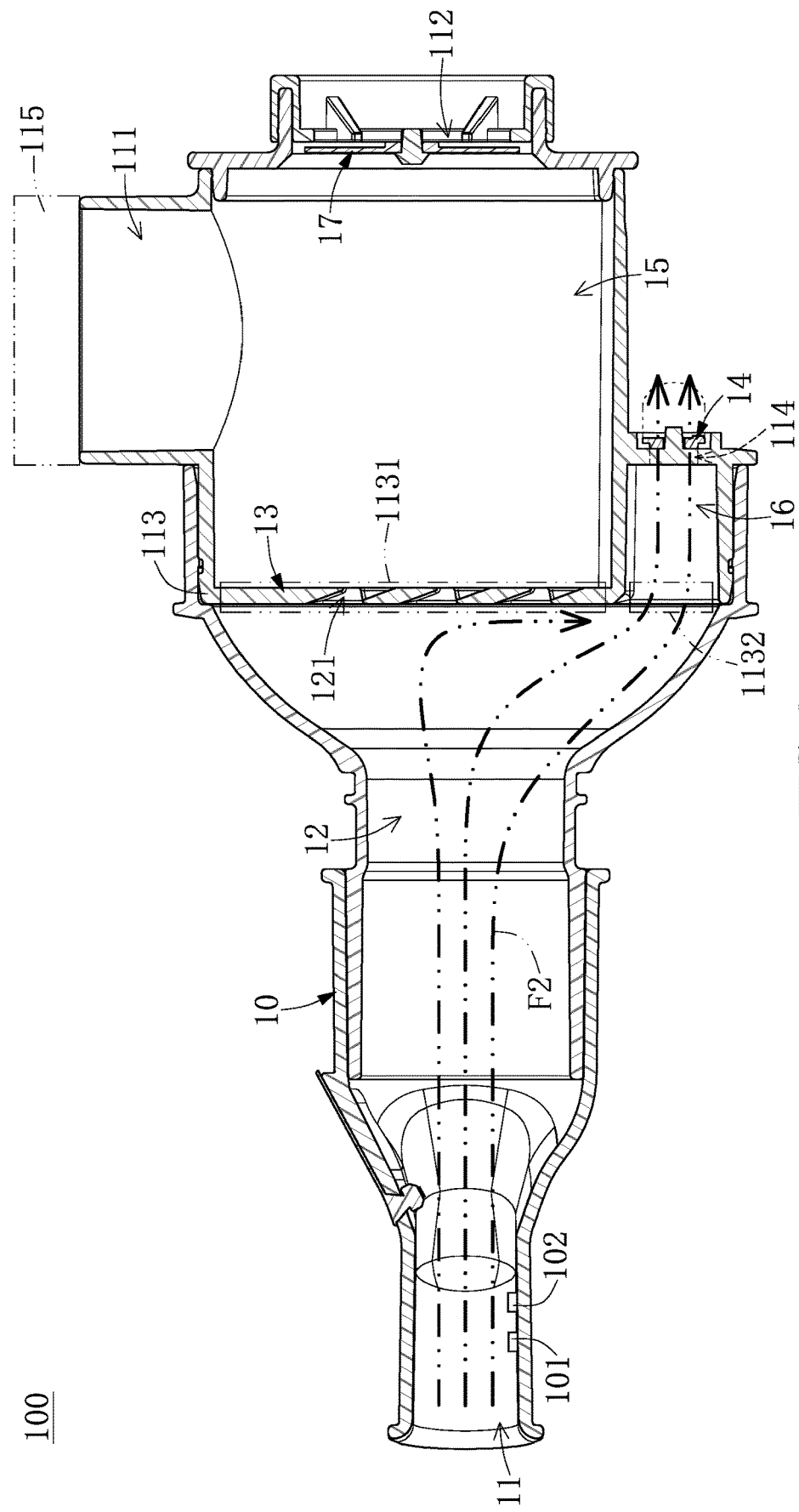
FIG. 2 is another schematic sectional view showing the structure of the nebulizer according to one embodiment of the disclosure.
Figure 5:
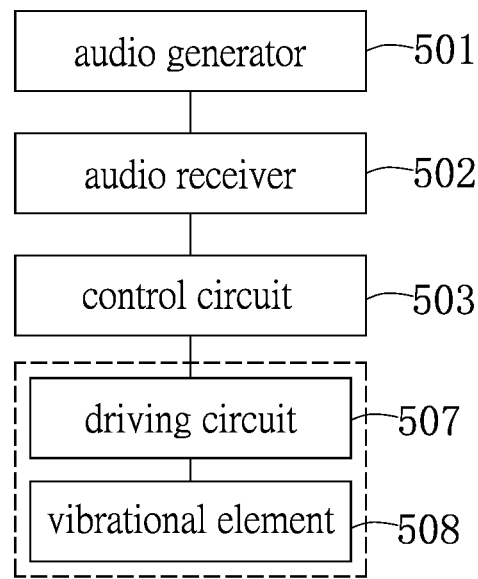
FIG. 5 is a block diagram depicting a circuit system that is configured to produce an aerosol in one embodiment of the disclosure.

Reference is made to FIG. 5, which shows the circuit system for driving the nebulizer to produce the aerosol, in which the nebulizer includes the audio generator (101, 302) and the audio receiver (102, 303) illustrated in FIGS. 1, 2 and 3.

The nebulizer has an audio generator 501 and an audio receiver 502 disposed on the path of airflow in the nebulizer. The audio generator 501 generates the acoustic waves that can be driven by the airflow. The audio generator 501 can be configured to generate the acoustic waves having the audio signals specified to be within a specific frequency range. The audio receiver 502 is such as a microphone that can be disposed on the path where the airflow flows in the nebulizer. The audio receiver 502 can be configured to receive the waves with any specific frequency, for example, acoustic waves with a frequency that the human ear can hear or cannot hear.

The circuit system includes a control circuit 503, which is electrically connected to the audio receiver 502 and the aerosol generator (i.e., a driving circuit 507). The control circuit 503 controls operations of the nebulizer, including determining whether or not to drive the aerosol generator to produce an aerosol in response to the audio signals obtained from the acoustic waves. For producing the aerosol, the driving circuit 507 is used to drive a vibrational element 508 to generate vibration waves so as to nebulize a substance. The control circuit 503 is mainly used to control the nebulizer according to the audio signals and volume obtained from the user's inhalation and exhalation. The control circuit 503 can adjust an operating time to drive the aerosol generator or even provide a time delay according to practical conditions.

Figure 6:
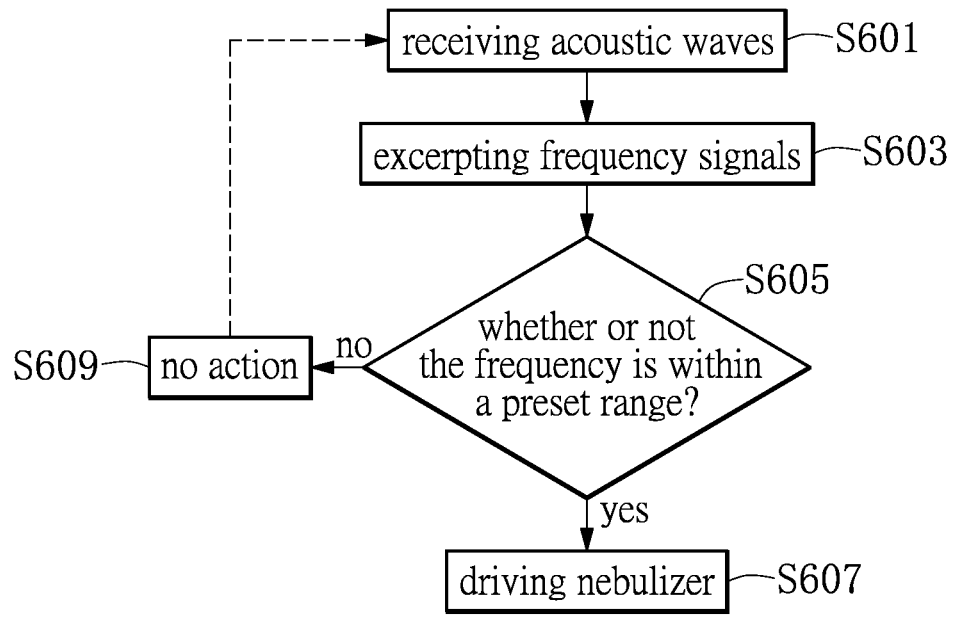
FIG. 6 shows a flow chart describing a method for driving the nebulizer according to one embodiment of the disclosure.

Reference is made to FIG. 6, which shows a flow chart describing the method for driving the nebulizer according to one embodiment of the present disclosure.

In the beginning, in step S601, the audio receiver disposed in the nebulizer receives acoustic waves that can be from an ambient environment or the airflow in the nebulizer. In step S603, a processing routine executed in the control circuit can be used to process the acoustic waves for excerpting audio signals from the acoustic waves. Afterwards, such as in step S605, the processing routine can compare the frequency signals obtained from the audio signals with a predetermined frequency range. If it is determined that the audio signals match the condition set by the predetermined frequency range, such as in step S607, the control circuit generates a driving signal to activate the driving circuit for driving the nebulizer. For example, a vibrational element is driven to generate a voltage that drives an aperture element to be vibrated. The vibration waves can nebulize the substance on the aperture element, and the aerosol is produced. Conversely, if the audio signals do not match the condition, such as in step S609, the circuit system may discard these signals, and the routine can continue with receiving of the acoustic waves (e.g., the step S601).

After repeating the above steps, the nebulizer continues to operate based on airflows produced by the user's breathing.

Figure 7:
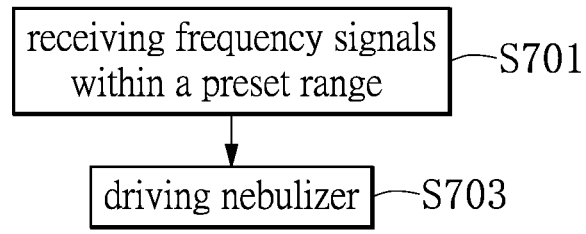
FIG. 7 shows another flow chart describing the method for driving the nebulizer according to one embodiment of the disclosure.

FIG. 7 shows a flow chart describing the method for driving the nebulizer having an audio receiver configured to receive sound within a specific frequency range according to one embodiment of the disclosure. The audio receiver adopts a filtering technology for actively excluding the acoustic waves outside the range of audio signals accepted by the system. In step S701, when the audio receiver receives the audio signals within the present range, the control circuit is informed thereof. In step S703, the control circuit can directly drive the nebulizer to operate without additional determination.

Figure 8:
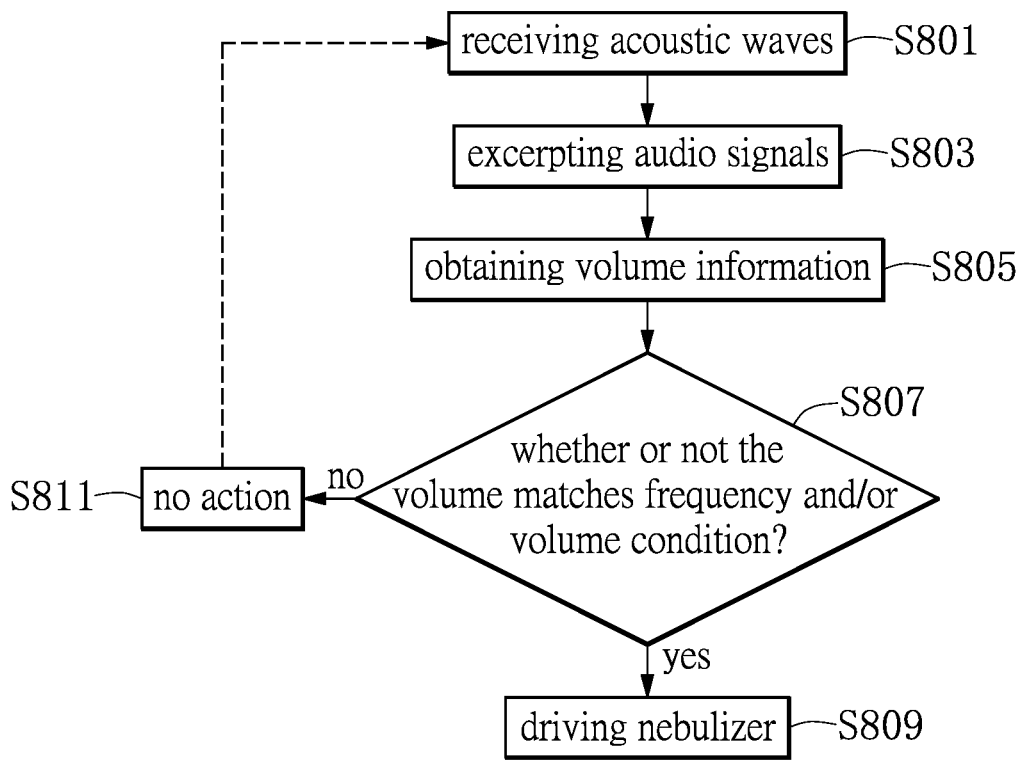
FIG. 8 shows yet another flow chart describing the method for driving the nebulizer according to one embodiment of the disclosure.

FIG. 8 shows a further flow chart describing the method for driving the nebulizer while incorporating volume obtained from the acoustic waves according to one embodiment of the disclosure.

In beginning, such as in step S801, the audio receiver receives acoustic waves. In step S803, a signal processing process, e.g., a Fourier transform, can be used to retrieve composition of the audio signals obtained from the acoustic waves. In step S805, a volume of the acoustic waves can be obtained.

Afterwards, in step S807, the control circuit determines whether or not the acoustic waves match conditions of predetermined thresholds (e.g., a frequency threshold and a volume threshold). Such conditions can refer to both the audio signals and the volume, or only the audio signals as mentioned in the above embodiments. In one further embodiment of the disclosure, the control circuit of the nebulizer can rely only on the volume to make the determination. When both the audio signals and the volume are referred to as the thresholds for determining whether or not to drive the nebulizer to operate, the control circuit determines whether or not the audio signals are within the predetermined frequency range and the volume is greater than the predetermined threshold. If both the audio signals and the volume meet the thresholds, such as in step S809, the control circuit generates a driving signal to activate the driving circuit to drive the nebulizer to operate. Conversely, if any of the audio signals or volume does not meet the threshold, such as in step S811, the control circuit can ignore the information obtained from the acoustic waves, and return to step S801 for repeating the steps such as receiving acoustic waves and obtaining the audio signals.

As mentioned in the above embodiments, the volume is related to the force of the inhalation or exhalation of the user. In step S807, the circuit system can rely on the volume as the only condition to determine whether or not to drive the nebulizer to produce the aerosol. When the volume meets the threshold, such as in step S809, the nebulizer is driven to produce the aerosol; otherwise, such as in step S811, the nebulizer does not operate since the volume does not meet the threshold. The nebulizer continues to operate based on the user's inhalation and exhalation while repeating the above steps.

It should be noted that the volume acts as a condition to determine whether or not to drive the nebulizer to operate because a loud volume or large amplitude of the acoustic waves indicates that the user intends to inhale the nebulized medicine produced by the nebulizer when the user uses his mouth to hold the nebulizer to breathe. In other words, the user would deliberately inhale with a force to form an airflow with a flow rate in the nebulizer when he wishes to take the medicine to be nebulized by the nebulizer. Therefore, the audio generator may generate a volume or amplitude that is loud enough to be received by the audio receiver, thus driving the nebulizer to operate. Conversely, when the inhalation of the user is unintentional or during the exhalation stage, the volume of the acoustic waves may not be enough to drive the nebulizer to operate once compared with the threshold. Further, an external airflow that flows into the nebulizer may be excluded since the volume of the external airflow does not meet the threshold.

Further, if the volume acts as a reference to determine whether or not to drive the nebulizer to operate, the amplitude of the waves forming the volume can also be used in the determination. The circuit system can control the vibration element to produce more aerosols by increasing an output rate if the volume is greater. Fewer aerosols may be provided if the volume is low but still meets the threshold. Therefore, the method achieves an effect of allowing the medicine to be dynamically administered.

Figure 9:
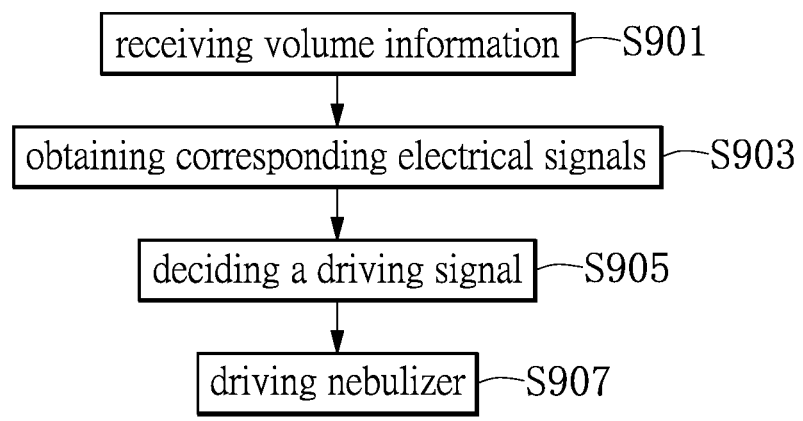
FIG. 9 shows still another flow chart describing the method for driving the nebulizer according to one embodiment of the disclosure.

FIG. 9 shows a flow chart describing the method for driving the nebulizer based on the volume in one embodiment of the disclosure. In the present example, the volume is referred to for deciding energy to drive the vibrational element.

In step S901, the control circuit obtains a volume of the acoustic waves received from the audio receiver. In step S903, the volume is used to obtain corresponding electrical information based on a predetermined scenario. For example, a lookup table can be incorporated herein. The lookup table is configured to record multiple operating modes of the nebulizer. In the lookup table, multiple volumes greater than the predetermined threshold correspond to multiple driving voltages, and each volume corresponds to a driving voltage that is used to initiate an operating mode. The lookup table can be stored in the control circuit of the nebulizer. In step S905, when the control circuit obtains a volume, a corresponding driving voltage is decided after querying the lookup table. In step S907, the driving voltage acts as a driving signal to activate the driving circuit to drive the nebulizer. The driving circuit can dynamically adjust an output rate in order to produce the aerosol.

The description of the flow chart shown in FIG. 9 can also be incorporated in the flow chart shown in FIG. 6. When the acoustic waves are obtained, the volume can also be acquired. In addition to being a reference to determine whether or not to drive the nebulizer to operate, the volume can also be referred to in deciding an operating mode of the nebulizer. By referring to FIG. 7, the audio receiver can be configured to receive the acoustic waves within a predetermined frequency range, and the audio receiver can filter out the acoustic waves outside the predetermined frequency range. Further, the nebulizer can be driven to operate when not only the audio receiver receives the acoustic waves within the predetermined frequency range, but the condition of the volume also meets the threshold.

In conclusion, according to the above embodiments of the method for driving the nebulizer and the circuit system of the nebulizer, the nebulizer allows the user to inhale the nebulized medicine. For example, when the user holds the breathing element of the nebulizer in his mouth to inhale and exhale, inhalation and exhalation airflows are generated in the nebulizer. The nebulizer can utilize the inhalation airflow to generate the audio signals (or in cooperation with the volume) for driving the aerosol generator. Alternatively, the exhalation airflow can be used to generate the audio signals for turning off (i.e., not driving) the nebulizer. Therefore, the nebulizer can operate more effectively and is capable of preventing unnecessary waste.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for driving a nebulizer, comprising:
   receiving a unidirectional airflow passing through the nebulizer by an audio generator which is a device or a structure specified to generate audio signals within a predetermined frequency range and configured to be driven by a single-direction airflow;
   driving the audio generator to generate acoustic waves within the predetermined frequency range;
   receiving the acoustic waves via an audio receiver of the nebulizer; and
   determining, by a control circuit, whether or not the nebulizer is driven to produce an aerosol in response to audio signals obtained from the acoustic waves;
   wherein the control circuit drives an aerosol generator of the nebulizer to produce the aerosol when the audio signals are within the predetermined frequency range.

2. The method according to claim 1, wherein the audio receiver is configured to receive the audio signals that are specified to be within the predetermined frequency range.

3. The method according to claim 1, wherein, when the audio signals obtained from the acoustic waves are received, a volume of the acoustic waves is also obtained so as to determine whether or not the nebulizer generates the aerosol according to the audio signals and the volume.

4. The method according to claim 3, wherein, when the audio signals are within the predetermined frequency range and the volume is greater than a predetermined threshold, the control circuit drives the aerosol generator to produce the aerosol.

5. The method according to claim 4, wherein the aerosol generator includes a vibrator which generates the aerosol by vibration.

6. The method according to claim 5, wherein the control circuit controls vibration amplitude or vibration frequency of the vibrator according to the volume so as to control an output rate for producing the aerosol.

7. A circuit system disposed in a nebulizer for driving the nebulizer, comprising:
   an audio generator, which is a device or a structure specified to generate audio signals within a predetermined frequency range and configured to be driven by a single-direction airflow to generate acoustic waves within the predetermined frequency range when receiving a unidirectional airflow passing through the nebulizer;
   an audio receiver used to receive the acoustic waves and being disposed on a path along which the airflow passes in the nebulizer;
   an aerosol generator used to produce an aerosol; and
   a control circuit that is electrically connected to the audio receiver and the aerosol generator, and that is used to control operations of the nebulizer, including determining whether or not to drive the nebulizer to produce the aerosol in response to the audio signals obtained from the acoustic waves;

wherein the control circuit drives the aerosol generator of the nebulizer to produce the aerosol when the audio signals generated by the audio generator are within the predetermined frequency range.

8. The circuit system according to claim 7, wherein, when the audio receiver receives the acoustic waves, the audio signals are obtained from the acoustic waves and a volume of the acoustic waves is also obtained, so as to determine whether or not the nebulizer generates the aerosol according to the audio signals and the volume.

9. The circuit system according to claim 7, wherein the audio receiver is configured to receive the audio signals that are within a predetermined frequency range.

10. The circuit system according to claim 9, wherein, when the audio receiver receives the acoustic waves, the audio signals are obtained from the acoustic waves and a volume of the acoustic waves is also obtained, so as to determine whether or not the nebulizer generates the aerosol according to the audio signals and the volume.

11. The circuit system according to claim 10, wherein, when the audio signals are within the predetermined frequency range and the volume is greater than a predetermined threshold, the control circuit drives the aerosol generator to produce the aerosol.

12. The circuit system according to claim 11, wherein the aerosol generator includes a vibrator which generates the aerosol by vibration.

13. The circuit system according to claim 12, wherein the control circuit controls vibration amplitude or vibration frequency of the vibrator according to the volume so as to control an output rate for producing the aerosol.

14. The circuit system according to claim 7, wherein the audio generator includes a reed or an acoustic structure that is configured to allow the airflow to generate the audio signals within the predetermined frequency range.

15. The circuit system according to claim 14, wherein the predetermined frequency range is a common frequency range detectable by a human ear, or an ultrasonic frequency range undetectable by the human ear.

16. The method according to claim 1, wherein the audio generator includes a reed that is configured to allow the airflow to generate the audio signals within the predetermined frequency range.

* * * * *